United States Patent [19]

Van Horn

[11] 4,034,078

[45] July 5, 1977

[54] PRODUCT AND METHOD FOR CONTROLLING ODORS

[75] Inventor: Earl Thomas Van Horn, Manchester, Mo.

[73] Assignee: Ralston Purina Company, St. Louis, Mo.

[22] Filed: Sept. 22, 1975

[21] Appl. No.: 615,616

Related U.S. Application Data

[63] Continuation of Ser. No. 115,788, Feb. 16, 1971, abandoned.

[52] U.S. Cl. .................................. 424/76; 424/94
[51] Int. Cl.$^2$ ................ A61K 37/48; A61L 13/00
[58] Field of Search ........................... 424/94, 76

[56] References Cited

OTHER PUBLICATIONS

Chem. Abst., vol. 25, 4016$^5$, (1931).

*Primary Examiner*—Stanley J. Friedman
*Attorney, Agent, or Firm*—Virgil B. Hill; Veo Peoples, Jr.

[57] ABSTRACT

A synergistically effective composition with improved odor abatement properties has been devised which comprises a mixture of an enzyme, preferably a proteolytic enzyme, and a ferrous salt composition. The composition is particularly effective in reducing noxious odors emanating from waste materials by spreading the composition over the waste material. It also provides a process for the effective control of animal waste odors in commercial animal raising operations such as cattle feedlots, swine parlors, poultry operations, or the like, without affecting the usefulness of the waste material as fertilizer.

7 Claims, No Drawings

PRODUCT AND METHOD FOR CONTROLLING ODORS

This is a continuation of application Ser. No. 115,788, filed Feb. 16, 1971, now abandoned.

BACKGROUND OF THE INVENTION

This invention relates to a composition and process for controlling obnoxious odor emanation from various substances.

Air pollution control and specifically odor abatement is a matter of increasing public concern and, accordingly, an effective means of abating or reducing obnoxious odors has become a much sought for goal. A particular problem with odor control or odor abatement is with successful elimination of various odoriferous materials emanating from chemical products, fermentation processes, and especially animal waste or by-products. Animal waste products have long presented a disposal problem and the problem has become more pronounced as the fattening of large numbers of cattle, swine or poultry in commercial feedlots or grow out operations has become a more common and important practice. Likewise, the large quantities of animal excretion produced in such a commercial feedlot provide a potential for a severe atmospheric odor problem, although the same problem exists on a smaller scale on farms in general and even around the home with domesticated animals or pets. Thus, animal waste products have presented a unique and difficult odor abatement problem, and one which has been largely unsolved satisfactorily by the prior art. For example, lime oxidizing agents, such as potassium permanganate, or paraformaldehyde, have been used to abate odor on both a small scale and on a larger scale such as exists in industrial manufacturing and in agriculture with feedlots, poultry production, etc. While most such agents have had some degree of effectiveness, they have generally not been considered to be a complete solution to the problem since the effect of some has been short lasting and not enough to overcome the most severe conditions of odor pollution.

The odors which emanate from materials such as animal waste may be either ammoniacal in character or also be putrefactive in nature as a result of enzymatic decomposition of the organic matter which is present. Both forms of odors must be effectively controlled in order to generally control the odor pollution problem in industry, particularly with the argiculture industries which produce a large amount of animal waste material in the raising of animals and care therefore. As previously noted, various chemical treatments as have been proposed by the prior art have generally not been entirely effective in quickly eliminating the odors as well as for an extended period of time. However, other various means of treating the animal wastes to reduce odor pollution. besides chemical means, such as submersion under water, ventilation techniques, and also frequent removal of the wastes has not only been less than successful, but has been difficult to implement as a program in large animal feeding operations such as cattle feedlots or poultry operations which may produce extremely large quantities of animal waste. For example, a cattle feedlot may have a population of from 2,000 to as much as 100,000 head during a peak season. The cattle are retained in the feedlot for about 5 months; during this period of time, the average size animal may produce as much as 26 pounds of waste per day. Accordingly, mechanical treatment or periodic removal of such quantities of waste is a formidable task. Therefore, chemical treatment of the waste material as it lies on the ground is preferable to reduce odors until the waste material can be conveniently and economically removed. Thus, the longer the period of time odor abatement results by chemical treatment, the more advantageous it is from the standpoint of economy since it is necessary to dispose of the waste material at only periodic intervals.

The present invention, therefore, has been found to be an effective means of controlling noxious odors in general, and specifically those as are encountered in agriculture and with the raising of animals in feedlots, poultry operations or in and around farms, although the composition is also useful in the removal of odors from air recirculation systems or similar odor removal problems.

SUMMARY OF THE INVENTION

The present invention relates to a combination of materials to create a composition with a resultant effect to odor abatement which is unexpectedly greater than would be obtained when either material is used singularly to abate odors. The composition comprises a combination of an enzyme, preferably a proteolytic enzyme, and a ferrous salt composition. This composition has been unexpectedly found to produce a synergistic effect between its components and provide an improved means of abating noxious odors produced by odor producing substances, but especially animal waste, for an extended period of time. The use of this composition provides a process by which chemical treatment of animal waste material can be made by scattering or spreading the composition over the waste material or odor causing substance in an effective amount and, therefore, reduce noxious odors to an acceptable level.

The composition is particularly significant in providing a process for the abatement of noxious odors resulting from animal waste material in large animal facilities such as feedlots, poultry houses, or similar operations for the commercial raising of animals. The composition, insofar as its use in such facilities, provides a chemical treatment means of abating odor from waste material or other odor causing substances until convenient disposal of the waste material can be carried out.

The composition is also significant in that, while reducing odor to an acceptable level, it consists of materials which do not render the waste material unusable as fertilizer, since the ingredients of the composition are in general materials which do not destroy the usefulness of the waste material as fertilizer, but are also nutrients as are found in rich soil. Thus, they improve the waste material's usefulness as a fertilizer, while rendering it odor free.

It is, therefore, an object of the present invention to provide for a composition comprising an enzyme and a ferrous salt composition which has been unexpectedly found to have marked deodorant properties for an extended period of time with many practical applications in odor abatement and which has been found particularly useful for abation of noxious odors produced by animal waste material.

It is also an object of the present invention to provide a process for the chemical treatment of waste or odoriferous material and render it odor free until convenient disposal thereof may be made, which comprises scattering in an effective amount, the aforementioned composition over the waste material to result in complete odor abatement for an extended period of time, or until removal of the waste material may be made.

DESCRIPTION OF THE PREFERRED EMBODIMENTS

The present invention comprises a composition and the use thereof as an odor control means for substances emanating noxious odors, in particular, animal waste material.

The composition which we have found to be so effective in providing long lasting odor abatement of animal wastes, most generally comprises a dried mixture of an enzyme, preferably a proteolytic enzyme, and a ferrous salt composition. This composition has been found to have unexpected, long lasting deodorant properties resulting from a synergistic effect from its components which makes it very suitable for elimination of noxious odors arising from odoriferous material.

The composition has numerous practical applications, although being particularly suitable for rendering animal waste or human waste materials odor free. For example, it could be used in an atmospheric or air recirculation system for removal of stale or noxious odors and many other types of similar applications.

The enzyme component of the present novel composition is preferably a protease or proteoltyic enzyme as may be derived from a variety of sources. It is not critical to the practice of the present invention that the protease be any particular or specific enzyme, and therefore various crude and unrefined mixtures of the proteases may be employed with equal effectiveness. The deodorant effect seems to result from the ferrous salt compositions and an enzyme in general, rather than from a combination of a specific protease and a specific ferrous salt, therefore, various commercial unrefined grade mixtures of proteases containing minor amounts of amylases or celluloses such as for example, having a proteolytic value per gram or PVU activity above about 50,000 PVU/gm, may be conveniently and readily utilized in the process of the present invention. The proteolytic enzyme family, in general, are those enzymes which act to hydrolyze and reduce proteins and, by way of example, include various specific enzymes such as papain, ficin, bromelin, and others. Although proteolytic enzymes are considered preferred for the practice of the present process, various other families of enzymes may be singularly employed or used in combination with a protease mixture as a major or minor component thereof. Such other enzymes include the amyloytic and cellulytic families of enzymes with these classes of enzymes being those which are especially capable of acting on various carbohydrates such as starches and cellulose. A PVU or proteolytic value unit is defined as the quantity by weight of an enzyme which digests 1 mg of casein to a standard turbidity endpoint (70% Transmission at 420 millimicrons with a ⅞ inch tube and an Evelyn Colorimeter) in one hour at 37° C. and at a pH of 7.0.

Since the composition of the present invention may be dispersed as a dry powder over the material to be deodorized, the enzyme which is employed should be preferably dried or in a dried condition for admixing with the ferrous salt composition to form the deodorant composition of the present invention.

The ferrous salt composition which is used as the other major ingredient of the present novel composition for odor abatement, may be selected from a wide variety of ferrous salts and may include mixtures of various ferrous salts. In general, the anion component, radical or radicals of the ferrous salt composition employed is not critical to its effectiveness in the present composition. However, anion radicals, which are readily ionizable, as for example sulfate, nitrate, chloride, acetate, lactate and citrate, are preferred as opposed to other anion radicals derived from organic acids or acid donors which are essentially water insoluble in nature.

The ferrous salt composition employed in the present invention may be a single ferrous salt or may be approximately a mixture of various salts. A specific ferrous salt is unnecessary although various ferrous salts, or mixtures thereof, which have an anion component derived from a readily ionizable acid donor, are preferred.

To form the composition of the present invention, the enzyme is added to the ferrous salt composition in an amount to provide an enzymatic activity in the salt composition of at least about 120,000 proteolytic value units per lb., preferably about 340,000 proteolytic value units per lb. Although greater amounts of the enzyme may be employed, the addition of the enzyme above the optimum level does not cause a substantial increase in odor abatement to justify the cost of adding an additional amount of enzyme.

The balance of the composition is a ferrous salt composition, as has been found effective for odor abatement. The metallic salt composition may be only a single ferrous salt, although mixtures of various ferrous salts may also be used to form the salt composition.

It is preferable, however, that the ferrous salt composition be a single material rather than a mixture, although the preference for such a material rather than a mixture is an economic limit rather than a limit in effectiveness, since some divalent metallic salts such as ferrous sulfate are particularly suitable since it is commercially available as the by-product of various processes and is accordingly cheaper than some of the other salts noted to be effective or mixtures of these.

The purity of either the salt composition or the enzyme is generally not critical insofar as providing for effective odor abatement by the composition. In general, the salts employed will have a purity above about 95% by weight although a high degree of purity is unnecessary for good deodorant properties or for use in the present composition. As noted, the enzyme may also be of a crude unrefined nature and still provide a synergistic effect when used in combination with a ferrous salt composition in the odor abatement composition of the present invention.

To use the composition of the present invention for reducting unpleasant odors emanating from substances, especially animal waste, the composition may be spread or scattered as a dry powder on an event basis at an application rate of at least about 2 lbs per 100 sq. ft., preferably 5 – 15 lbs per 100 sq. ft. The composition may be conveniently applied by dusting or scattering over the waste material. It should be understood, of course, that there is really not a maximum application rate since this is dependent on the severity of the problem and that large quantities of waste material may require a higher treatment rate particularly if the odor pollution problem is severe. The use of the composition in the preferred amount causes a pronounced reduction in odor from odor causing material and, furthermore, retains this effect up to a period which can be as much as 14 to 21 days depending on the quantity of waste material or weather conditions.

The most unexpected result of using the present composition to abate odors, especially waste material, was the prolonged effect which was obtained by using the enzyme in combination with the ferrous salt composition; this effect was in addition to an immediate sequestration of odors when the composition is applied. When the composition of the present invention is employed, not only does immediate odor abatement occur, but the duration of odor abatement of the composition will be two to three times greater than results if either the enzyme or ferrous salt is employed by itself.

One of the most unexpected aspects of the present invention was the failure to attain improved odor abatement properties when other metallic salts having known deodorant properties were tried in combination with an enzyme as in the present invention. Not only was there a failure to produce an increase in activity, but there was even a reduction in activity of some of the metallic salts by adding an enzyme thereto. Examples of some of the other metallic salts with which no synergistic results were obtained include Cupric, zinc, managenese, ferric and aluminum salts. It, therefore, may be seen that enhanced odor abatement activity which is obtained by combining an enzyme and a ferrous salt is both unexpected and unique in character.

It is, therefore, believed that the present composition has certain unexpected qualities which overcome disadvantages of the prior art in providing for chemical treatment of waste material. Not only does immediate odor abatement of waste material occur, but its effective duration is longer than most single chemical treatment means previously described by the prior art.

The use of such a composition which has a strong and durable effect on odor abatement provides a process for handling of animal waste material which has a number of advantages over the prior art. With an effective, yet long lasting, chemical treatment means, the waste material may be treated while it lies on the ground and yet produce no odor pollution problem. This allows periodic rather than daily removal of waste material and the elimination of a formidable task when large quantities of waste material are involved as in a commercial feeding operation. Furtermore, the composition as used to provide an effective chemical treatment means does not render the waste material unusable as fertilizer since the materials used in the present composition do not destroy or render unavailable nitrogeneous materials in the waste material and may be easily assimilated by the soil without a harmful effect thereon.

The following examples will be illustrative of my invention.

EXAMPLE 1

The odor abatement activity of a ferrous salt composition with various levels of an enzyme added thereto was evaluated on a measured quantity of animal waste material. The odor abatement effect attained with these combinations were compared against two control samples, one sample being a ferrous salt, specifically ferrous sulfate, and the second control sample being a proteolytic enzyme. Compositions comprising ferrous sulfate and a proteolytic enzyme were formulated and designated as samples A, B, C, D and E. The composition of each of these samples is set forth in the following Table 1:

TABLE 1

| SAMPLE | AMOUNT OF ENZYME (PVU/LB) | % FERROUS SULFATE BY WEIGHT |
| --- | --- | --- |
| A | 340,000 | 90 |
| B | 272,000 | 92 |
| C | 204,000 | 94 |
| D | 136,000 | 96 |
| E | 68,000 | 98 |

Results were obtained on the five samples, with five replications for each sample, the sample comprising a mixture of an enzyme and a ferrous salt in comparison to controls of ferrous sulfate and an enzyme used by themselves. This was done by placing approximately ¼ lb. of fresh chicken manure in a closed pint jar followed by the addition of the various combinations and the controls at a predetermined application rate of 15 lb./100 sq. ft. The ammonia which was present in the atmosphere of the closed jar was measured to provide an objective measurement of the intensity of the noxious odor emanating from the animal waste material. Periodic samplings at different time intervals over a period of time up to 22 days were made of the air of the jar to determine approximate ammonia concentration as the jars were stored at room temperature. The ammonia concentration was measured by using the Vineland$_R$ ammonia quick testing kit sold by Vineland Laboratories Incorporated, Vineland, New Jersey. This utilizes measurement of alkalinity of the air as an indication of the presence and quantity almmonia gas, and provides a rapid objective measurement of ammonia concentration in the atmosphere of the closed jar or container. The device generally has an upper limit of detection for ammonia of about 50 ppm; therefore, levels greater than this were not objectively measured.

Results of the test were as follows and set forth in Table 2.

TABLE 2

| SAMPLE | NO. OF REPLICATIONS | AMMONIA CONCENTRATION (ppm) | | NO. OF DAYS OF ACTIVITY |
| --- | --- | --- | --- | --- |
| | | PRE-TREATMENT | POST-TREATMENT AVG (ALL DAYS) | |
| Ferrous Sulfate (Control) | 5 | >50 | 29 | 5 |
| Enzyme (Control) | 5 | >50 | 21 | 12 |
| A | 5 | >50 | 18 | 21 |
| B | 5 | >50 | 20 | 12 |
| C | 5 | >50 | 23 | 12 |
| D | 5 | >50 | 26 | 12 |
| E | 5 | >50 | 26 | 12 |

It may be seen that an enhancement in odor abatement occurs as measured by the post-treatment average ammonia concentration in all of the combinations containing an amount of added enzyme when compared against ferrous sulfate used by itself. It may also be seen that an optimum level of odor abatement both in terms of reduction of activity, as well as duration of activity, occurred with Sample A. It may be seen that the duration of activity for Sample A is better than three times that for the same weight of ferrous salt by itself and is almost twice that of the same weight of enzyme used by itself.

EXAMPLE 2

A composition which comprised a mixture of a ferrous salt and an enzyme was added to animal waste material at different application rates to determine the effectiveness thereof. The composition had an enzyme present in an amount of about 340,000 PVU/lb. which was about 10% by weight of the composition, the balance of the composition was ferrous sulfate. Testing of the composition at different application rates was carried out by using ¼ lb. of fresh chicken manure added to a pint jar, and periodic measurement over the period of 10 days was made of the atmosphere to determine odor level. The ammonia concentration was measured to provide an objective odor measurement technique and this was done by the technique as set forth in Example 1. The results of this test when the composition was used at different application rates with five replications of each sample is set froth in Table 3.

ployed or when ferrous sulfate was employed by itself. The proteolytic enzyme was added to the ferrous sulfate in an amount to achieve an enzymatic activity in the composition of about 340,000 PVU/lb.

The field test was conducted in a building housing swine and specifically in three concrete floored pens with dimensions of 10 × 10 within the building. At the time the test was conducted, there were six market-size hogs in each pen, each hog weighing about 200 lbs. Ammonia concentration was measured as set forth in Example 1 and was used as an objective index of one form of noxious odor emanating from the droppings. The putrefactive odor emanating from the droppings was also subjectively measured by two independent observers, each smelling the putrefactive odor and then scoring or assigning a number dependent onthe severity of the putrefactive odor as measured by a numerical scale from 0 to 3. 0 was adjudged to be no odor, 1 was adjudged to be a light odor, 2 was judged to be moderate odor, and 3 was used to indicate a severe odor.

Droppings were allowed to accumulate in each pen until the ammonia concentration was above 50 ppm as measured by the ammonia quick testing kit, and a putrefactive odor score of 3 or higher was attained by the two independent observers. At this time, one of the pens was treated with ferrous sulfate by itself, another pen was treated with the aforementioned composition which comprised a mixture of ferrous sulfate and an

TABLE 3

| | | | AMMONIA CONCENTRATION (ppm) | | |
|---|---|---|---|---|---|
| SAMPLE | APPLICATION RATE | NO. OF REPLICATIONS | PRE-TREATMENT (AVG.) | POST-TREATMENT (AVG.) | NO. OF DAYS ACTIVITY |
| A | 15 lb/100 sq ft | 5 | >50 | 24 | 9 |
| B | 10 lb/100 sq ft | 5 | >50 | 32 | 3 |
| C | 5 lb/100 sq ft | 5 | >50 | 39 | 2 |
| D | 4 lb/100 sq ft | 5 | >50 | 40 | 1 |
| E | 3 lb/100 sq ft | 5 | >50 | 41 | 1 |
| F | 2 lb/100 sq ft | 5 | >50 | 45 | 1 |
| Control | 0 lb/100 sq ft | 5 | >50 | >50 | 0 |

It may be seen that the best application rate occurs both in duration and intensity of odor abation with 15 lb/100 sq. ft., although the lower application rates also abated odor activity to a significant degree when measured against a control to which no composition was added.

EXAMPLE 3

The odor control composition which comprises a mixture of ferrous sulfate and a proteolytic enzyme was field tested to evaluate the effectiveness of this composition as used in the field and as compared to results which were obtained when no composition was employed or when ferrous sulfate was employed by itself.

enzyme, and the third pen was left untreated to serve as a control. Each pen was treated at a predetermined application rate of 15 lb/100 sq. ft. Application of the compositions to the droppings in the pen was acomplished with the use of a hand scoop and by distributing as evenly as possible over the droppings on the floor.

Ammonia readings and putrefactive scores were recorded daily for a period of 14 days when the test was concluded. Four ammonia measurements were taken for each pen and then averaged to obtain the daily ammonia concentration in each pen.

Results of this test are set forth in Table 4.

TABLE 4

| | | AMMONIA CONCENTRATION (ppm) | | | | | | | | | | | |
|---|---|---|---|---|---|---|---|---|---|---|---|---|---|
| TREATMENT | USE LEVEL | PRE-TMT. | DAY 1 | DAY 2 | DAY 3 | DAY 4 | DAY 5 | DAY 6 | DAY 7 | DAY 8 | DAY 9-14 | POST TMT. AVG. | NO. DAYS SHOWING ACTIVITY |
| control (no treatment) | — | 50 | 50 | 35 | 35 | 27 | 20 | 20 | 20 | 20 | 20 | 27 | — |
| Ferrous Sulfate | 15 lbs/100 sq. ft. | 50 | 0 | 0 | 2 | 9 | 20 | 20 | 20 | 20 | 20 | 13 | 4 |
| Ferrous Sulfate & Enzyme | 15 lbs/100 sq. ft. | 50 | 0 | 0 | 0 | 7 | 15 | 17 | 17 | 17 | 20 | 11 | 8 |
| | | PUTREFACTIVE ODOR SCORE | | | | | | | | | | | |
| control (no treatment) | — | 3 | 3 | 3 | 3 | 3 | 3 | 3 | 3 | 3 | 3 | 3 | — |
| Ferrous Sulfate | 15 lbs/100 sq. ft. | 3 | 0 | 0 | 0 | 1 | 2 | 2 | 2 | 2 | 2 to 3 | 1.4 | 12 |
| Ferrous Sulfate & Enzyme | 15 lbs/100 | 3 | 0 | 0 | 0 | 1 | 1 | 1 | 1 | 1 | 1 to 3 | 0.9 | 13 |

TABLE 4-continued

| TREATMENT | USE LEVEL sq. ft. | PRE-TMT. | DAY 1 | DAY 2 | DAY 3 | DAY 4 | DAY 5 | DAY 6 | DAY 7 | DAY 8 | DAY 9-14 | POST TMT. AVG. | NO. DAYS SHOWING ACTIVITY |
|---|---|---|---|---|---|---|---|---|---|---|---|---|---|

It may be seen that from the test that a significant increase in amount and duration of odor abatement occurred when a mixture of the enzyme and a ferrous salt was employed as compared to the ferrous salt being used by itself, or in comparison to the untreated pen. It should be recognized that an increase in both intensity and duration of odor abatement occurred relative to both ammoniacal and putrefactive odors. Thus, the present composition was found to effectively control the two major forms of odors which emanate from waste material as compared to the untreated control pen and also exhibit a synergistic effect as compared to the ferrous salt by itself.

EXAMPLE 4

The odor control composition which comprises a mixture of ferrous sulfate and a proteolytic enzyme was field tested to evaluate the effectiveness of this composition as used in the field and as compared to results which were obtained when no composition was employed or when ferrous sulfate was employed by itself. The proteolytic enzyme was added to the ferrous sulfate in an amount to achieve an enzymatic activity in the composition of about 340,000 PVU/lb.

The field test was conducted in a building housing swine and specifically in three concrete floored pens with dimensions of 10' × 10' within the building. At the time the test was conducted, there were eight feeder pigs in each pen, each pig weighing about 65 lbs. Ammonia concentration was measured as set forth in Example 1 and was used as an objective index of one form of noxious odor emanating from the droppings. The putrefactive odor emanating from the droppings was also measured subjectively by two independent observers, each smelling the putrefactive odor and then scoring or assigning a number dependent on the severity of the putrefactive odor as measured by a numerical scale from 0 to 3.

Droppings were allowed to accumulate in each pen until the ammonia concentration was about 20 ppm as measured by the ammonia quick testing kit, and a putrefactive odor score of 3 or higher was attained by the two independent observers. At this time, one of the pens was treated with ferrous sulfate by itself, another pen was treated with the aforementioned composition which comprised a mixture of ferrous sulfate and an enzyme, and the third pen was left untreated to serve as a control. Each pen was treated at a predetermined application rate of 15 lb/100 sq. ft. Application of the compositions to the droppings in the pen was accomplished with the use of a hand scoop and by distributing as evenly as possible over the droppings on the floor.

Ammonia readings and putrefactive scores were recorded daily for a period of 14 days when the test was concluded. Four ammonia measurements were taken for each pen and then averaged to obtain the daily ammonia concentration in each pen.

Results of this test are set forth in Table 5.

TABLE 5

| TREATMENT | USE LEVEL | PRE-TMT. AVG. | DAY 1 | DAY 2 | DAY 3 | DAY 4 | DAY 5 | DAY 6 | DAY 7 | DAY 8 | DAY 9 | DAY 10 | DAY 14 | POST TMT. AVG. | NO. DAYS SHOWING ACTIVITY |
|---|---|---|---|---|---|---|---|---|---|---|---|---|---|---|---|
| AMMONIA CONCENTRATION (ppm) | | | | | | | | | | | | | | | |
| Control (no treatment) | — | 18 | 20 | 20 | 20 | 20 | 20 | 20 | 20 | 20 | 20 | 20 | 20 | 20 | 0 |
| Ferrous Sulfate | 15 lbs/100 sq ft | 20 | 1 | 1 | 10 | 10 | 12 | 17 | 20 | 20 | 20 | 20 | 20 | 14 | 8 |
| Ferrous Sulfate & Enzyme | 15 lbs/100 sq ft | 20 | 0 | 0 | 7 | 10 | 10 | 10 | 12 | 17 | 17 | 20 | 20 | 11 | 11 |
| PUTREFACTIVE ODOR SCORE | | | | | | | | | | | | | | | |
| Control (no treatment) | — | 3 | 3 | 3 | 3 | 3 | 3 | 3 | 3 | 3 | 3 | 3 | 3 | 3 | |
| Ferrous Sulfate | 15 lbs/100 sq ft | 3 | 1 | 1 | 1 | 1 | 1 | 2 | 2 | 2 | 2 | 2 | 3 | 1.6 | |
| Ferrous Sulfate & Enzyme | 15 lbs/100 sq ft | 3 | 1 | 1 | 1 | 1 | 1 | 1.5 | 1.5 | 2 | 2 | 2 | 3 | 1.5 | |

It may be seen from the results of the test, in terms of ammonia concentration in particular, that the combination of an enzyme and ferrous salt significantly reduced ammonia odors under the conditions of the test, below that which was obtained when no treatment was used or when ferrous sulfate was employed by itself. This is shown by a reduction in both ammonia concentration and in length or duration of odor abatement. The putrefactive odor score between ferrous sulfate used by itself and the composition was generally similar although in both cases, it was significantly better than the untreated controlled pen.

EXAMPLE 5

The odor control composition which comprises a mixture of ferrous sulfate and a proteolytic enzyme was field tested to evaluate the effectiveness of this composition as used in the field and as compared to results which were obtained when no composition was employed or when ferrous sulfate was employed by itself. The proteolytic enzyme was added to the ferrous sulfate in an amount to achieve an enzymatic activity in the composition of about 340,000 PVU/lb.

The field test was conducted in a building which housed caged layer hens and comprised three rows of caged layers with concrete dropping pits below each row. The dropping pits were about 4 × 25, and at the time the test was conducted, there was a density of 60 laying hens above each concrete dropping pit. Ammonia concentration was measured as set forth in Example 1 and was used as an objective index of the principal noxious odor which emanated from the droppings. The putrefactive odor was not measured since the odor was observed to be primarily ammoniacal in nature.

Droppings were allowed to accumulate in each pit until the ammonia concentration was above 50 ppm as measured by the ammonia quick testing kit. At this time, one of the pits was treated with ferrous sulfate by itself, another pit was treated with a composition which comprised a mixture of ferrous sulfate and an enzyme, and the third pit was left untreated to serve as a control. Each pit was treated at a predetermined application rate of 15 lb/100 sq. ft. Application of the compositions to the droppings in the pit was accomplished with the use of a hand scoop and by distributing as evenly as possible over the droppings on the floor.

Ammonia readings were recorded daily for a period of 14 days when the test was concluded. Eight ammonia measurements were taken for each pit each day and then averaged to obtain the daily ammonia concentration in each pit.

Results of this test are set forth in Table 6.

TABLE 6

| TREATMENT | USE LEVEL | AMMONIA CONCENTRATION (ppm) | | | | | | | | | | | POST TMT. AVG. | NO. DAYS SHOWING ACTIVITY |
|---|---|---|---|---|---|---|---|---|---|---|---|---|---|---|
| | | PRE-TMT. AVG. | DAY 1 | DAY 2 | DAY 3 | DAY 4 | DAY 5 | DAY 6 | DAY 7 | DAY 8 | DAY 9 | DAY 10 | | |
| Control (no treatment) | — | 50 | 50 | 39 | 28 | 31 | 28 | 20 | 20 | 20 | 20 | 20 | 27.6 | 0 |
| Ferrous Sulfate | 15 lbs/100 sq ft | 50 | 8 | 6 | 11 | 16 | 20 | 20 | 20 | 20 | 20 | 20 | 16.1 | 5 |
| Ferrous Sulfate & Enzyme | 15 lbs/100 sq ft | 50 | 8 | 5 | 8 | 13 | 14 | 15 | 20 | 20 | 20 | 20 | 14.3 | 6 |

The above Ammonia Concentrations (ppm) are the average of eight (8) counts taken per treatment per 0.4.

It may be seen from the results of the test on caged layers, and as measured by ammonia concentration, that an effective and enhanced degree of odor abatement occurs when a composition containing ferrous sulfate and a proteolytic enzyme is employed. It may be noted that in terms of both intensity and in duration of activity, was a synergisitc or enhanced effect noted from the combination as compared to the control of ferrous sulfate being used by itself and at the same application rate. While both treatments were significantly better than the control to which no treatment was made, it may be seen that the composition exhibits a synergistic response as compared to ferrous sulfate by itself.

It is my intention to set forth in the appended claims all such equivalents or modifications as may reasonably be included within their scope.

I claim:

1. A method for the abatement of noxious odors emanating from an odoriferous substance comprising: treating said substance with an effective amount of a mixture which comprises a substantially proteolytic enzyme in an amount by weight of said mixture sufficient to yield an enzymatic activity of about 340,000 PVU/lb. and a ferrous salt, so that a synergistic deodorizing effect is achieved with said mixture thereby abating said odors.

2. A method as set forth in claim 1 wherein said salt has a anion component derived from a readily ionizable acid donor.

3. A method as set forth in claim 2 wherein said acid donor is selected from the group consisting of an inorganic acid and a water soluble organic acid.

4. A method as set forth in claim 1 wherein said substance is treated with at least about 2 lb./100 sq. ft. of said mixture.

5. A method as set forth in claim 1 wherein said substance is treated with between about 5-15 lb./100 sq. ft. of said mixture.

6. A method for the abatement of noxious odors comprising: treating said odors with an effective amount of a mixture which comprises a substantially proteolytic enzyme in an amount by weight of said mixture sufficient to yield an enzymatic activity of about 340,000 PVU/lb. and a ferrous salt, so that a synergistic deodorizing effect is achieved with said mixture, thereby abating said odors.

7. A method as set forth in claim 6 wherein said salt comprises ferrous sulfate.

* * * * *